(12) United States Patent
Braun et al.

(10) Patent No.: US 7,282,120 B2
(45) Date of Patent: Oct. 16, 2007

(54) UV-ACTIVATED CHLORINATION PROCESS

(75) Inventors: Max Braun, Wedemark (DE); Kerstin Eichholz, Langenhagen (DE); Stefan Palsherm, Barsinghausen (DE); Carsten Brosch, Hannover (DE)

(73) Assignee: Solvay Fluor GmbH, Hannover (DE)

( * ) Notice: Subject to any disclaimer, the term of this patent is extended or adjusted under 35 U.S.C. 154(b) by 0 days.

(21) Appl. No.: 11/008,109

(22) Filed: Dec. 10, 2004

(65) Prior Publication Data

US 2005/0101811 A1    May 12, 2005

Related U.S. Application Data

(63) Continuation of application No. 10/627,755, filed on Jul. 28, 2003, now abandoned, which is a continuation of application No. 10/016,127, filed on Dec. 17, 2001, now abandoned, which is a continuation of application No. PCT/DE00/01953, filed on Jun. 14, 2000.

(30) Foreign Application Priority Data

Jun. 16, 1999  (DE) ................. 199 27 394

(51) Int. Cl.
C07B 63/00    (2006.01)
C07C 17/00    (2006.01)

(52) U.S. Cl. ................ 204/158.21; 204/157.94

(58) Field of Classification Search ............ 204/157.94, 204/158.21
See application file for complete search history.

(56) References Cited

U.S. PATENT DOCUMENTS

| | | | |
|---|---|---|---|
| 4,060,469 A | 11/1977 | Sweeney et al. | 204/163 R |
| 5,336,377 A | 8/1994 | Yates et al. | 203/29 |
| 5,421,971 A | 6/1995 | Puy et al. | 204/157.6 |
| 5,944,962 A * | 8/1999 | Bradford | 204/157.94 |
| 5,951,830 A * | 9/1999 | Bertocchio et al. | 204/157.15 |

FOREIGN PATENT DOCUMENTS

| | | |
|---|---|---|
| CN | 1097189 A | 1/1995 |
| CN | 1097189 A * | 1/1995 |
| EP | 0 143 864 | 6/1985 |
| EP | 0407989 | 1/1991 |
| GB | 698127 | 10/1953 |
| GB | 2318350 | 4/1998 |
| JP | 49041166 | 12/1969 |
| WO | 93/12058 | 6/1993 |
| WO | 97/37955 | 10/1997 |

OTHER PUBLICATIONS

Muller et al., "Die Photochemischen Chlorierungun von Cis-Dichlorathylen zu Tetrachlorathan und von Trichlorathylen zu Pentachlorathan", Z. Physik. Chem. B (no month, 1937), pp. 455-461.*

Mueller et al., "Die photochemischen Chlorierungen von cis-Dichloraethylen zu Tetrachloraethan und von Trichloraethylen zu Pentachloraethan." Z. Phys. Chem. Abt. B, 465-461 (1937), no month.

The International Search Report dated Dec. 14, 2000.

* cited by examiner

*Primary Examiner*—Edna Wong
(74) *Attorney, Agent, or Firm*—Crowell & Moring LLP

(57) ABSTRACT

A method of producing alkanes containing chlorine by addition of chlorine to C—C double bonds or C—C triple bonds or by exchange of hydrogen for chlorine by contacting the starting compound in the gas or liquid phase with elemental chlorine and irradiating the reaction mixture with UV light having a wavelength of $\lambda \geq 280$ nm. In this way pentachloroethane can be produced from trichloroethylene, CFC-113 from HCFC-123 or HFC-133a, CFC-112a from HCFC-142b, or HCFC-123 from HCFC-133a. The method also is suitable for separating photochlorinatable impurities from HFC-365-mfc to obtain purified HFC-365-mfc. Advantages include high yields and excellent selectivity.

8 Claims, No Drawings

UV-ACTIVATED CHLORINATION PROCESS

CROSS REFERENCE TO RELATED APPLICATIONS

This application is a continuation of application Ser. No. 10/627,755, filed Jul. 28, 2003, now abandoned, which is a continuation of application Ser. No. 10/016,127, filed Dec. 17, 2001, now abandoned, which in turn is a continuation of international patent application no. PCT/DE00/01953, filed Jun. 14, 2000 designating the United States of America, the entire disclosure of which is incorporated herein by reference. Priority is claimed based on Federal Republic of Germany patent application no. DE 199 27 394.4, filed Jun. 16, 1999.

BACKGROUND OF THE INVENTION

The invention relates to a process for producing certain chlorine-containing alkanes through UV-light supported chlorination.

It has long been known that elemental chlorine under incident light radiation will attach to unsaturated carbon compounds or that an exchange of hydrogen for chlorine will occur.

SUMMARY OF THE INVENTION

It is an object of the invention to provide a new process for producing chlorine-containing alkanes.

Another object of the invention is to provide a process for producing chlorine-containing alkanes with a high reaction rate and high selectivity.

These and other objects are achieved in accordance with the present invention as described and claimed hereinafter.

The process according to the invention for producing chlorine-containing alkanes selected from the group consisting of pentachloroethane, 1,1,1,-trifluoro-2,2,2-trichloroethane, 1,1,1-trifluoro-2,2-dichloroethane and 1,1,1,2-tetrachloro-2,2-difluorothane by attaching chlorine to starting compounds with C—C double bonds or by exchanging hydrogen for chlorine, and for producing purified 1,1,1,3,3-pentafluorobutane from 1,1,1,3,3-pentafluorobutane that has been contaminated with compounds with C—C double bonds or C—C triple bonds by chlorinating these unsaturated compounds, provides that the starting compound in the gas or the liquid phase is brought into contact with elemental chlorine and is irradiated with UV light with a wavelength of $\lambda \geq 280$ nm.

It is possible to work in the liquid phase or in the gas phase. Generally, one can work at a temperature ranging from room temperature to 200° C. and at a pressure of 1 to 10 bar (absolute). The reaction temperature and the pressure are selected in such a way that the starting compound to be treated, or the starting mixture, is present in the gas phase or the liquid phase. One variant of the invention concerns its use as a production process. Another variant concerns its use as a purification process. The use as a production process will first be described in greater detail.

Particularly preferably, the process is used to produce pentachloroethane from trichloroethylene, to produce 1,1,1,2-tetrachloro-2,2-difluoroethane from 1-chloro-1,1-difluoroethane, and to produce 1,1,1-trifluoro-2,2,2-trichloroethane from 1,1,1-trifluoro-2,2-dichloroethane.

The molar ratio of starting compound to elemental chlorine ranges from 1:0.1 to 1:10 when attaching chlorine and from 1:0.01 to 1:5 when exchanging hydrogen for chlorine.

If only one of two H atoms is to be exchanged in the exchange of hydrogen for chlorine, the ratio of starting compounds to chlorine falls in the upper range (lower chlorine content). Preferably, the chlorine is used in an amount that is 0.9 times to 1.3 times the stoichiometrically required amount.

Another variant of the invention concerns the purification of 1,1,1,3,3-pentafluorobutane (HFC-365mfc) with the aim of separating photochlorinatable olefinic impurities. It has been shown that the olefinic impurities, which are production-related, can essentially be selectively converted by the inventive photochlorination and separated in a simplified manner in the form of chlorination products.

For irradiation, it is advantageous to use radiation lamps (e.g., Philips fluorescent tubes) that only emit (UV) light of a wavelength at or above 280 nm ($\lambda \geq 280$ nm). In such case, it is possible to irradiate through quartz glass. The only prerequisite for this variant is that these lamps emit in the absorption range of the elemental chlorine. Alternatively, it is possible to use radiation lamps (e.g., Hg medium or high-pressure discharge lamps), which also emit some lines in the range below 280 nm ($\lambda < 280$ nm). In this variant, irradiation has to occur through a glass that is transparent only for light with a wavelength of 280 nm or above ($\lambda > 280$ nm), i.e., that filters out the shorter wave radiation component of $\lambda < 280$ nm. Well suited are, for instance, borosilicate glasses. This type of glass typically contains 7 to 13% $B_2O_3$, 70 to 80% $SiO_2$, furthermore 2 to 7% $Al_2O_3$ and 4 to 8% $Na_2O+K_2O$ and 0 to 5% alkaliine-earth metal oxides. Known trademarks for borosilicate glasses are Duran, Pyrex and Solidex. It is of course also possible to proceed by using on the one hand a radiation lamp that emits light above the indicated wavelengths and, in addition, glasses that are transparent for light above the indicated wavelength (i.e., that are non-transparent for light below the indicated wavelength).

Also suitable for irradiation are lamps, e.g., Hg high-pressure discharge lamps, which due to a dopant emit primarily, or only, in the wavelength range at or above 280 NM. Hg high-pressure discharge lamps, for instance, have a rather intensive band in the range of 254 nm which is filtered out, e.g., by borosilicate glass, as described above. In Hg high-pressure discharge lamps that are doped with metal iodides, this line is strongly suppressed. Surprising in these doped lamps is the frequently more than proportional increase in the conversion rate. Excellent results with respect to conversion rate and selectivity are obtained with Hg high-pressure discharge lamps that are doped with gallium iodide and especially with lamps that are doped with thallium iodide or cadmium iodide. Even with the use of this type of lamp, it is preferable to use glass that filters out the shorter wave radiation component of $\lambda \leq 280$ nm. It is suitable and technically advantageous to use the entire radiation range with wavelengths above and below said limits.

HFC-365mfc can be purified in the liquid phase or in the gas phase. Pentachloroethane is advantageously produced in the liquid phase. CFC-112a, CFC-113a and HCFC-123 are advantageously produced in the gas phase. Continuous operation is especially facilitated by working in the gas phase.

In the gas phase, the process is advantageously conducted in a flow-through apparatus. The starting material (the corresponding hydrogen and halogen-containing starting compounds and chlorine) is continuously fed into the flow-through apparatus and the reaction product is continuously withdrawn in proportion to the amount introduced.

The average residence time in the reaction vessel is preferably between 0.01 and 30 minutes, preferably between 0.01 and 3 minutes, particularly preferably between 0.5 and 3.0 minutes. Good results can be achieved even if the residence times are very short, e.g., between 0.04 and 0.5 minutes. The optimum average residence time, which depends, among other things, on the lamp output and on the geometric parameters of the radiation apparatus (flow-through apparatus) can be determined by simple manual tests and analysis of the product stream, e.g., by gas chromatography.

Better conversion rates and higher selectivity can be achieved by using, instead of a single radiation lamp with a certain output, two or more lower-output lamps with an equivalent total output in reactors that are connected in series. The product is then advantageously separated after leaving the corresponding reactions, e.g., by freezing it out. Proper swirling of the reaction mixture, e.g., by suitable installations in the reactor, is also often advantageous. In the liquid phase, it is preferred to work in batches. The process has the advantages of high conversion at high selectivity.

The following examples are intended to illustrate the invention in greater detail without limiting its scope.

EXAMPLES 1 to 6

Production of 1,1,1-trifluoro-2,2,2-trichloroethane (CFC-113a) through photochlorination of 1,1,1-trifluoro-2,2-dichloroethane (HCPC-123) through Duran 50 with light with a wavelength of $\lambda > 280$ nm.

Apparatus: double shell glass reactor (double shell for oil heating) with a submersible shaft made of Duran® 50 (400 ml reaction volume), equipped with a submersible Hg discharge lamp TQ 718 by Heraeus-Noblelight with water cooling. The 1,1,1-trifluoro-2,2-dichloroethane was evaporated with a pre-evaporator and was introduced from below as a gas into the reactor together with the chlorine (mixed). The product stream exited at the top. The reaction temperature was 110° C. The gas stream exiting the reactor was analyzed by gas chromatography (GC) (sampling in the gas collection tube).

| Tests 1 to 6 conducted with different chlorine feeds: | | | |
|---|---|---|---|
| Test | mole % Chlorine | Conversion Rate | 113a Selectivity |
| 1 | 10 | 3.79 | 99.13 |
| 2 | 30 | 5.18 | 99.04 |
| 3 | 60 | 17.41 | 97.7 |
| 4 | 90 | 31.94 | 98.29 |
| 5 | 120 | 80.63 | 95.9 |
| 6 | 150 | 100 | 97.3 |

* Analysis data provided in GC surface percent

EXAMPLES 7 TO 11

Comparison Test

Production of 113a by Photochlorination of 123 Through Quartz Glass

Apparatus: double shell glass reactor (double shell for oil heating) with submersible shaft made of quartz glass (400 ml reaction volume) equipped with submersible Hg discharge lamp TQ 718 of Heraeus Noblelight with water cooling. The 1,1,1-trifluoro-2,2-dichloroethane was evaporated and introduced from below as a gas into the reactor together with the chlorine. The product stream exited at the top. The reaction temperature was 110° C.

| Tests 1 to 5 conducted with different chlorine feeds: | | | |
|---|---|---|---|
| Test | mole % Chlorine | Conversion Rate | 113a Selectivity |
| 7 | 10 | 1.44 | 96.4 |
| 8 | 30 | 13.5 | 95.64 |
| 9 | 60 | 13.4 | 90.1 |
| 10 | 90 | 26.64 | 93.5 |
| 11 | 120 | 77.24 | 79.17 |

* Analysis data provided in GC surface percent

EXAMPLE 12

Removal of Olefinic Byproducts from 1,1,1,3,3-pentaflurobutane (365mfc) Through Photochlorination with $\lambda > 280$ nm a) Laboratory Tests 50 g samples of 365 mfc contaminated with 7,000 ppm $C_4ClF_3H_4$ (two isomers) were disposed, respectively, in two 100-ml Duran® 50 glass flasks and agitated.

Thermal Test:

Immediately after adding 0.4 g (5.6 mmole) chlorine, the one flask was wrapped in aluminum foil. After 24 h the sample was examined by gas chromatography. Out of the 7,000 ppm $C_4ClF_3H_4$ (2 isomers), 4,450 ppm were still detected, but the 365mfc content was reduced by well over 1%.

Photochemical Test:

The second flask, after adding 0.2 g (2.8 mmole) chlorine, was irradiated overnight with a Philips fluorescent lamp (Philips reflector lamp No. 1099415, 40 W output). Subsequently, the sample was examined by gas chromatography. Out of the 7,000 ppm $C_4ClF_3H_4$ (2 isomers), 160 ppm were still detected, but the 365mfc content was almost unchanged. A further addition of 0.2 g (2.8 mmole) chlorine and irradiation overnight resulted in an amount of $C_4ClF_3H_4$ that was no longer detectable (<0.1 ppm, SIM run, GS-MSD), again with a nearly constant 365mfc content.

b) Technical Test

Test setup: Pfaudler reactor (V=100 l) with mounted glass column with top cooler (water cooling). In the cover of the Pfaudler reactor, a submersible Hg discharge lamp TQ 718 by Heraeus Noblelight was installed with a submersible tube made of Duran 50 glass. Irradiation thus took place at a wavelength of $\geq 280$ nm. The output was adjusted to 700 W.

Procedure: The 365mfc was pumped into the Pfaudler reactor. One half hour prior to chlorine metering, the submersible Hg discharge lamp (700 watt) was turned on while mixing. Through a submersible tube, approximately 20 l/h of chlorine were added until no olefins could be detected in the SIM run of the GC-MSD. After chlorination was completed, the submersible Hg discharge lamp was operated for another hour. The 365mfc thus treated was discharged and precision distilled in a distillation column (height: 3 m, diameter 100 mm, filled with 10 mm Raschig glass packing).

Test 12.1: 62.3 kg educt treated with 40.9 g chlorine/test duration 3 hours.

GC analysis of educt (before photochlorination): 99.5 w/w % 365mfc,
Total $C_4ClF_3H_4$: 0.112 w/w %
GC analysis of product (after photochlorination): 99.4 w/w % 365mfc,
Total $C_4ClF_3H_4$: <10 ppm Test 12.2: 62.0 kg educt treated with 110.9 g chlorine/test duration 5 hours.
Analysis of educt: 99.7% 365mfc,
Total $C_4ClF_3H_4$: 0.210%
Analysis of product: 99.6 w/w % 365mfc,
Total $C_4ClF_3H_4$: <10 ppm Purification: The fractions obtained from the tests were combined and precision distilled in the glass column. Their purity after distillation was 99.98% w/w % 365mfc.

EXAMPLE 13

Production of Pentachloroethane (120) from Trichloroethylene Through Photochlorination with λ>280 nm a) Photochlorination Test on a 5 l Scale Test setup: A 5 liter double shell vessel of Duran 50 glass with mounted reflux condenser, bubble counter and submersible tube with diffuser. The vessel also contained a water-cooled cooling coil. The vessel was irradiated from the outside with a Philips fluorescent tube (Philips reflector lamp No. 1099415, 40 Watts output).

Procedure: 3.24 kg (24.7 moles) trichloroethylene were filled into the vessel and heated to 60° C. (thermostat, connected to double shell). Subsequently, 1.926 kg (27.17 moles) chlorine was metered such that no chlorine was penetrating through or exiting the apparatus through the bubble counter. The reaction was completed after 3 hours.

Purification: The resulting pentachloroethane had a 99.4% degree of purity (rest: unconverted trichloroethylene and hexachloroethane) and can be used without further purification.

b) Technical Photochlorination Test

Test setup: Pfaudler reactor (V=100 l) with mounted glass column with top cooler (water cooling). In the cover of the Pfaudler reactor, a submersible Hg discharge lamp TQ 718 by Heraeus Noblelight was installed with a submersible tube made of Duran® 50 glass. Irradiation thus took place at a wavelength of λ>280 nm. The output was adjusted to 500 Watts.

Procedure: 65.7 kg (507 mole) trichloroethylene was filled into the Pfaudler reactor and heated to 60° C. and mixed. Subsequently, after lighting and burning in the lamp, 35.36 kg (500.1 mole) chlorine was introduced such that the chlorine did not penetrate through.

Purification: At the end of the test, without any further purification, the pentachloroethane produced had a degree of purity of 99.1% (GC %); remainder: trichloroethylene and hexachloroethane.

EXAMPLE 14

Comparison Example

Thermal Chlorination

14a) Thermal Chlorination of Trichloroethylene 50 g (0.381 mole) trichloroethylene was combined with 28 g (0.423 mole) chlorine in a 250 ml Roth autoclave and placed into an oil bath preheated to 100° C. When an internal temperature of about 50° C. was reached, marked exothermia developed and the autoclave content was discharged through the bursting disk into the outlet.

14b) Thermal Test on a 5 Liter Scale

Test setup: A 5 liter double shell vessel of Duran 50 glass with mounted reflux condenser, bubble counter and submersible tube with diffuser. The vessel also contained a water-cooled cooling coil. The apparatus was completely covered with aluminum foil.

Procedure: 3.24 kg (24.7 mole) trichloroethylene was introduced into the vessel and heated to 60° C. (thermostat, connected to double shell). Subsequently, 1.926 kg (27.17 mole) chlorine was metered such that no chlorine was penetrating through or exiting the apparatus via the bubble counter. After 15 hours, the introduction of chlorine was completed.

Purification: The resulting pentachloroethane had a purity of 83.3% (residue: unconverted trichloroethylene and large amounts of hexachloroethane).

EXAMPLES 15 TO 19

Production of 1,1,1-triffluoro-2,2-dichloroethane (123) from 1,1,1-trifluoro-2-chloroethane (133a) through photochlorination with λ>280 nm.

General Setup and Execution for Tests 15 to 19:

A mixture of 94.8 g (0.80 mole) 133a and a variable amount of chlorine were mixed and introduced in the form of a gas into a photochemical reactor holding 4.3 liters (diameter 100 mm, wall thickness 2 mm) made of Duran® 50. The reaction temperature during the 30-minute tests was 40° C. Irradiation was effected by 3×40 W UV lamps from Philips, type "Cleo Performance R-UVA 40 Watts" The lamps were cylindrically arranged around the photochemical reactor. The tests were evaluated by GC analysis of the reactor exhaust gas.

EXAMPLE 15

| Feed: | 94.8 g (0.80 mole) 133a, 5.67 g (0.08 mole) chlorine |
| --- | --- |
| Result: | Conversion: 13.98% |
| | Selectivity 123: 86% |
| | Selectivity 113a: 13% |

EXAMPLE 16

| Feed: | 94.8 (0.80 mole) 133a, 17.01 g (0.24 mole) chlorine |
| --- | --- |
| Result: | Conversion: 25.2% |
| | Selectivity 123: 74% |
| | Selectivity 113a: 26% |

EXAMPLE 17

| Feed: | 94.8 (0.80 mole) 133a, 34.03 g (0.48 mole) chlorine |
| --- | --- |
| Result: | Conversion: 38.8% |
| | Selectivity 123: 57.4% |
| | Selectivity 113a: 42% |

EXAMPLE 18

| Feed: | 94.8 (0.80 mole) 133a, 51.05 g (0.08 mole) chlorine |
|---|---|
| Result: | Conversion: 45.8% |
| | Selectivity 123: 47% |
| | Selectivity 113a: 53% |

EXAMPLE 19

| Feed: | 94.8 (0.80 mole) 133a, 68.06 g (0.96 mole) chlorine |
|---|---|
| Result: | Conversion: 51% |
| | Selectivity 123: 44.3% |
| | Selectivity 113a: 56% |

EXAMPLE 20

Photochlorination of 142b to Produce 112a

The reaction was performed analogously to Examples 1 to 6. Conversion and yield were comparable to the results from the production of 113a.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for producing purified 1,1,1,3,3-pentafluorobutane from 1,1,1,3,3-pentafluorobutane that has been contaminated by unsaturated compounds comprising $C_4ClF_3H_4$ by chlorinating the unsaturated contaminating compounds, said process comprising the acts of:
   contacting the contaminated 1,1,1,3,3-pentafluorobutane with elemental chlorine and
   irradiating the 1,1,1,3,3-pentafluorobutane with UV light having a wavelength of $\lambda \geq 280$ nm in order to produce purified 1,1,1,3,3-pentafluorobutane.

2. A process according to claim 1, wherein the process is carried out in the liquid phase.

3. A process according to claim 1, wherein the process is carried out at a temperature in the range from room temperature to 200° C.

4. A process according to claim 1, wherein the process is carried out at an absolute pressure of 1 to 10 bar.

5. A process according to claim 1, wherein the contacting and irradiating acts convert the unsaturated compounds into chlorine-containing impurities, and the chlorine-containing impurities are then separated from the 1,1,1,3,3-pentafluorobutane.

6. A process according to claim 1, wherein the elemental chlorine is used in an amount that is 0.9 times to 1.3 times a stoichiometrically required amount.

7. A process according to claim 1, wherein the irradiating is conducted before contacting the contaminated 1,1,1,3,3-pentafluorobutane with elemental chlorine.

8. A process according to claim 1, wherein the irradiating is conducted before, during, and after the step of contacting the contaminated 1,1,1,3,3-pentafluorobutane with elemental chlorine.

* * * * *